United States Patent
Coogan et al.

(10) Patent No.: US 11,408,891 B2
(45) Date of Patent: Aug. 9, 2022

(54) IMAGING AGENT

(71) Applicant: University of Lancaster, Lancaster (GB)

(72) Inventors: Michael Peter Coogan, Lancaster (GB); Sarah Louise Allinson, Lancaster (GB); Daria Maria Kania, Lancaster (GB); Charlotte Meri Amber Farrow, Lancaster (GB); Jane Harmer, Lancaster (GB); Harriet Louise Steel, Lancaster (GB)

(73) Assignee: University of Lancaster, Lancaster (GB)

(*) Notice: Subject to any disclaimer, the term of this patent is extended or adjusted under 35 U.S.C. 154(b) by 366 days.

(21) Appl. No.: 16/603,547

(22) PCT Filed: Apr. 6, 2018

(86) PCT No.: PCT/GB2018/050926
§ 371 (c)(1),
(2) Date: Oct. 7, 2019

(87) PCT Pub. No.: WO2018/185493
PCT Pub. Date: Oct. 11, 2018

(65) Prior Publication Data
US 2021/0088524 A1    Mar. 25, 2021

(30) Foreign Application Priority Data
Apr. 7, 2017 (GB) .................. 1705679

(51) Int. Cl.
| | | |
|---|---|---|
| *G01N 33/58* | (2006.01) | |
| *C07F 13/00* | (2006.01) | |
| *C07F 15/00* | (2006.01) | |
| *C07K 5/02* | (2006.01) | |
| *G01N 21/64* | (2006.01) | |

(52) U.S. Cl.
CPC ........... *G01N 33/582* (2013.01); *C07F 13/00* (2013.01); *C07F 15/0086* (2013.01); *C07K 5/0215* (2013.01); *G01N 21/6428* (2013.01); *G01N 2021/6439* (2013.01)

(58) Field of Classification Search
CPC .... C07F 13/00; C07F 15/0086; C07K 5/0215; G01N 2021/6439; G01N 21/6428; G01N 33/582; G06F 11/3006; G06F 11/3438; G06F 11/3476; G06F 16/24547; G06F 21/31; G06F 21/604; G06F 21/6218; G06F 21/6227; G06F 21/6254; G06F 2221/2107; H04L 2463/083; H04L 63/0281; H04L 63/08; H04L 63/0884; H04L 63/101; H04L 63/102; H04L 63/104; H04L 63/105; H04L 63/1425; H04L 63/166; H04L 63/168; H04L 67/42; H04L 69/326; H04L 69/329
See application file for complete search history.

(56) References Cited

FOREIGN PATENT DOCUMENTS

WO    WO-2018185493 A1    10/2018

OTHER PUBLICATIONS

Full paper for Louie et al. Inorg. Chem. (2011) 50: 9465-9471; cited in the IDS filed Oct. 7, 2010 (Year: 2011).*
Registry file from STN; RN 1332832-10-6 downloaded Dec. 3, 2021 (Year: 2021).*
Full paper for Amoroso et al. New J. Chem. (2008) 32: 1097-1102 (Year: 2008).*
"International Application No. PCT/GB2018/050926, International Search Report and Written Opinion dated Jun. 22, 2018", (dated Jun. 22, 2018), 12 pgs.
"United Kingdom Application GB1705679.7, Search Report under Section 17(5) dated Feb. 12, 2018", (dated Feb. 12, 2018), 6 pgs.
Amoroso, Angelo J., et al., "3-Chloromethylpyridyl bipyridinefac-tricarbonyl rhenium: a thiol-reactive luminophore for fluorescence microscopy accumulates in mitochondria", New Journal of Chemistry, vol. 32(7), 2008, (2008), 1097-1102.
Coogan, M. P., et al., "Progress with, and prospects for, metal complexes in cell imaging", Chem Commun (Camb). Jan. 14, 2014; 50(4):384-99, (Jan. 14, 2014), 384-99.
Elbaz-Alon, Yael, et al., "The yeast oligopeptide transporter Opt2 is localized to peroxisomes and affects glutathione redox homeostasis", FEMS, Yeast Res., 14 (2014) 1055-1067, (Sep. 22, 2014), 1055-1067.
Fernandez-Moreira, V., et al., "Uptake and localisation of rhenium fac-tricarbonyl polypyridyls in fluorescent cell imaging experiments", Org Biomol Chem. Sep. 7, 2010; 8(17):3888-901, (Sep. 7, 2010), 3888-901.

(Continued)

*Primary Examiner* — Susan M Hanley
(74) *Attorney, Agent, or Firm* — Schwegman Lundberg & Woessner, P.A.

(57) ABSTRACT

The invention relates to platinum and rhenium complexes of formula (I) that may be used as imaging agents. In particular, the invention relates to imaging agents, for example imaging agents for use in the imaging of peroxisomes. Certain embodiments of the invention relate to compounds per se. Other embodiments relate to a process for the preparation of compounds and to the use of compounds as imaging agents. (Formula (I))

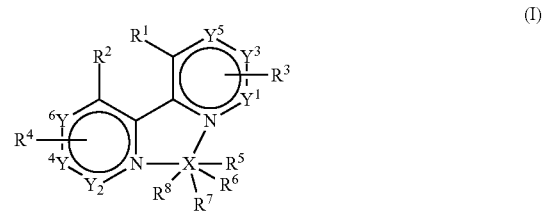

21 Claims, 4 Drawing Sheets

(56) References Cited

OTHER PUBLICATIONS

Jauregui, Miluska, et al., "Probing Peroxisome Dynamics and Biogenesis by Fluorescence Imaging", Current Protocols in Cell Biology, vol. 62, Issue 1, (Mar. 3, 2014), 21.9.1-21.9.20.
Lichtman, Jeff W., et al., "Fluorescence microscopy", Nature Methods, vol. 2, No. 12, (Dec. 2005), 910-919.
Lo, Kenneth Kam-Wing, et al., "Synthesis, Characterization, Photophysical Properties, and Biological Labeling Studies of a Series of Luminescent Rhenium(I) Polypyridine Maleimide Complexes", Inorganic Chemistry, 2002, 41, (2002), 40-46.
Louie, Man-Wai, et al., "Luminescent Rhenium(I) Polypyridine Fluorous Complexes as Novel Trifunctional Biological Probes", Inorg. Chem. 2011, vol. 50(19), (Aug. 30, 2011), 9465-9471.
Louie, Man-Wai, et al., "Synthesis, emission characteristics, cellular studies, and bioconjugation properties of luminescent rhenium(I) polypyridine complexes with a fluorous pendant", Organometallics, 31 (16), (Aug. 27, 2012), 5844-5855.
Smith, Jennifer J., et al., "Peroxisomes take shape", Nat Rev Mol Cell Biol. Dec. 2013; 14(12): 803-817, (Dec. 2013), 803-817.
Steel, Harriet L., et al., "Platinum trimethyl bipyridyl thiolates—new, tunable, red- to near IR emitting luminophores for bioimaging applications", Chem. Commun., 2015, 51(57), 11441, (Jun. 16, 2015), 11441-11444.
"International Application No. PCT/GB2018/050926, International Preliminary Report on Patentability dated Oct. 8, 2019", 8 pgs.

* cited by examiner

IMAGING AGENT

PRIORITY CLAIM TO RELATED APPLICATIONS

This application is a U.S. national stage filing under 35 U.S.C. § 371 from International Application No. PCT/GB2018/050926, filed on 6 Apr. 2018, and published as WO2018/185493 on 11 Oct. 2018, which claims the benefit under 35 U.S.C. 119 to United Kingdom Application No. 1705679.7, filed on 7 Apr. 2017, the benefit of priority of each of which is claimed herein, and which applications and publication are hereby incorporated herein by reference in their entirety.

FIELD OF THE INVENTION

The present invention relates to compounds and more particularly to compounds that may be used as imaging agents. In particular, the invention relates to imaging agents, for example imaging agents for use in the imaging of peroxisomes. Certain embodiments of the invention relate to compounds per se. Other embodiments relate to a process for the preparation of compounds and to the use of compounds as imaging agents.

BACKGROUND TO THE INVENTION

Fluorescence microscopy is one of the most powerful tools available for biologists and clinicians studying cells and cellular processes. Making use of fluorescence and phosphorescence, instead of or in addition to reflection and absorption, it gives high definition images (micron resolution) and can provide contrast between different components of the cell (Lichtman and Conchello, 2005, Fluorescence microscopy, Nature Methods Vol. 2, 910). The technique involves the addition of a dye or agent, known as a fluorophore, to a sample of cells. The fluorophore is able to absorb incident (excitation) light and subsequently emit light of a different wavelength (and hence different colour) which is detected by the microscope and used to generate the image. Advanced techniques such as confocal laser scanning microscopy allow rapid accumulation of emission intensity maps across two dimensional (2D) grids, and by acquiring layered or stacked series of these 2D grids, the series may be reconstituted into three dimensional (3D) images of the sample.

In order to identify components of the cell and to study cellular processes, fluorophores which target particular organelles (parts of the cell) are commonly used in these experiments. Sometimes, multiple fluorophores which emit different wavelengths (colours) of light are added to the same sample and, by detecting the emission from each fluorophore separately and then recombining the individual intensity maps, users can generate multi-coloured images with the different cellular components highlighted in contrasting colours (Pawley, J (Ed) 2006, Handbook of Biological Confocal Microscopy, Springer).

There are a large range of commercially available fluorophores for application in fluorescent microscopy (MolecularProbes Handbook 2010, ThermoFisher), some based on small molecules and some on fluorescent proteins. Fluorescent protein based agents require optimisation of transfection conditions for each cell line being used. Some cell types are very difficult to transfect, and there may be a lack of signal consistency due to variation of expression levels within a cell population, particularly under transient transfection conditions.

Moreover, over-expression of proteins beyond the levels normally found in cells can disrupt the very biological systems being studied. In contrast, small molecule probes have the advantages of being less biologically disruptive and having the convenience of "off-the-shelf" usability.

Most of the component organelles of cells can be targeted by a large range of different contrast agents, both protein based and small molecules, however there are no known small molecule agents that target peroxisomes, and there are only a small number of protein based agents available for imaging peroxisomes. Some of these commercially available agents include CellLight® Peroxisome-GFP for live cells, BacMam 2.0, Catalog number: 010604, 1 unit £340.08; SelectFX® Alexa Fluor® 488 Peroxisome Labeling Kit for fixed cells, 1 unit £480.90, both Invitrogen by ThermoFisher. The live cell agent is based on an expression vector for Green Fluorescent Protein (GFP) combined with a human peroxisomal C-terminal targeting sequence and works via the expression of fluorescent fusion protein. It therefore does not work in fixed cells. The fixed cell variation combines an Alexa Fluor® dye with an antibody which labels peroxisomal membrane protein 70 (PMP 70). Thus each of these is a large construct of either antibody or GFP and no economically viable small molecule variations are currently available.

Peroxisomes are important organelles that are responsible for chemical reactions involving the formation and subsequent reactions of hydrogen peroxide as part of oxidation of substrates and the cellular energy processes (Smith et al., 2013, Peroxisomes take shape, Nature Reviews Molecular Cell Biology, Vol. 14, 803). Incorrect function of, and/or proliferation of, peroxisomes are implicated in a number of serious medical conditions and the lack of readily available imaging agents for peroxisomes hinders the study of these conditions. The lack of small molecule imaging agents for peroxisomes is related to a lack of clear understanding of the uptake of small molecules by peroxisomes which has hindered the development of fluorescent tags for peroxisomes.

The use of bipyridyl platinum trimethyl [bpyPtMe$_2$] complexes in cellular imaging has been previously reported (Steel et al (2015), Platinum trimethyl bipyridyl thiolates new, tunable, red- to near IR emitting luminophores for bioimaging applications, *Chem, Commun., Vol.* 51, 11441) demonstrating that [bpyPtMe$_3$] complexes of sulphur ligands are fluorescent. A single example of these compounds (S-4-C$_6$—H$_4$—CO$_2$Me) has been shown to be taken up by cells but no specificity for any organelles was demonstrated and many different components were illuminated simultaneously.

A number of targeted imaging agents based on rhenium are also known (Coogan et al., 2014, Progress with, and prospects for, metal complexes in cell imaging, *Chem. Commun. Vol.* 50, 384) however none of these have been shown to target peroxisomes.

Thus there remains a need in the art for further small molecule imaging agents, and in particular there is an unmet need for small molecule imaging agents that target peroxisomes.

It is an aim of aspects of the present invention to at least partially mitigate the problems associated with the prior art.

It is an aim of certain embodiments of the invention to provide a compound for use as an imaging agent.

It is an aim of certain embodiments of the invention to provide a compound for use as an imaging agent for the imaging of certain cellular structures, for example peroxisomes.

It is an aim of certain embodiments of the invention to provide an imaging agent that specifically targets peroxisomes.

Surprisingly, a compound has now been developed that can be used as an imaging agent for the imaging of cellular structures, for example peroxisomes.

The inventors have found that compounds derivatized from glutathione (GSH) and metal complexes for example PtMe$_3$bpy or ReCO$_3$bpy (wherein bpy represents 2,2'-bipyridine and substituted analogues and related ligands such as 1,10-phenanthroline and dppz) result in imaging agents that are highly specific for peroxisomes.

It has been found that such agents are ideal for fluorescence microscopy having large Stokes shifts and in the case of the rhenium analogues long luminescence lifetimes. They work in both live and fixed cells, and show extremely low cytotoxicity (toxicity to cells) and phototoxicity (toxicity induced by light). This is important in long terms studies involving illumination with laser irradiation in confocal laser scanning microscopy applications. Whilst not wishing to be bound by theory, in is believed that the mechanism of uptake by peroxisomes is associated with the glutathione unit. Although glutathione is known to be incorporated by peroxisomes, the uptake pathway is unclear (Yael, et al, 2014, The yeast oligopeptide transporter Opt2 is localized to peroxisomes and affects glutathione redox homeostasis, FEMS Yeast Research, Vol. 14, 1055), and targeting imaging agents to peroxisomes using glutathione is believed to be hitherto unknown.

EMBODIMENTS OF THE INVENTION

In accordance with the present invention, there is provided an imaging agent, for example a fluorophore, comprising a glutathione ligand or a derivative thereof. Aptly, the imaging agent is a metal complex comprising a glutathione ligand or a derivative thereof. Aptly, the imaging agent is a platinum (Pt) or rhenium (Re) metal complex comprising a glutathione ligand or a derivative thereof. Aptly the imaging agent is for use in fluorescent microscopy.

In accordance with the invention, there is provided a compound of formula (I):

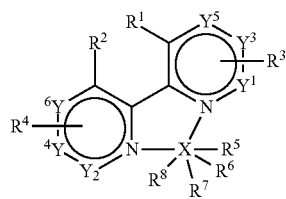

formula (I)

wherein:
X is selected from platinum and rhenium;
$Y^1$ is selected from —CH— and —N—;
$Y^3$ is —CH— or $Y^3$ is absent provided that when $Y^3$ is —CH—, $Y^5$ is selected from —CH— and —N—, and that when $Y^3$ is absent, $Y^5$ is —NR$^9$—;
$Y^2$ is selected from —CH— and —N—;
$Y^4$ is —CH— or $Y^4$ is absent provided that when $Y^4$ is —CH—, $Y^6$ is selected from —CH— and —N—, and that when $Y^4$ is absent, $Y^6$ is —NR$^{10}$—;

$R^1$ and $R^2$ are independently hydrogen or a substituent selected from $C_{1-10}$alkyl, halo, halo$C_{1-10}$hydroxy, hydroxy$C_{1-10}$alkyl, $C_{1-10}$alkoxy, $C_{1-10}$alkoxy$C_{1-10}$alkyl, nitro, nitro$C_{1-10}$alkyl, amino, $C_{1-10}$alkylamino, bis($C_{1-10}$alkyl)amino, amino$C_{1-10}$alkyl, bis($C_{1-10}$alkyl)amino$C_{1-10}$alkyl, aryl and heteroaryl wherein any alkyl, aryl and/or heteroaryl portion of a substituent is independently optionally substituted;

or $R^1$ and $R^2$ together with the atoms to which they are attached together form an optionally substituted ring system, for example a monocyclic, bicyclic or tricyclic ring system;

$R^3$ and $R^4$ are independently hydrogen or a substituent selected from $C_{1-10}$alkyl, halo, halo$C_{1-10}$alkyl, hydroxy, hydroxy$C_{1-10}$alkyl, $C_{1-10}$alkoxy$C_{1-10}$alkyl, nitro, nitro$C_{1-10}$alkyl, amino, $C_{1-10}$alkylamino, bis($C_{1-10}$alkyl)amino, bis($C_{1-10}$alkyl)amino$C_{1-10}$alkyl, aryl and heteroaryl wherein any alkyl, aryl and/or heteroaryl portion of a substituent is independently optionally substituted;

$R^5$, $R^6$ and $R^7$ are each independently selected from optionally substituted $C_{1-10}$alkyl, optionally substituted aryl, optionally substituted heteroaryl and —CO;

$R^8$ is glutathione or a derivative thereof (for example glutathione derived esters and amides and/or glutathione oxidised at S to S(O) and/or S(O)$_2$);

$R^9$ and $R^{10}$ are each independently selected from hydrogen and $C_{1-10}$alkyl; and wherein when any of the aforementioned alkyl, aryl and/or heteroaryl groups and/or ring systems are optionally substituted, the optional substituents, where chemically possible, are selected from 1 to 4 substituents which are independently, at each occurrence, selected from halo, nitro, cyano, $C_{1-10}$alkyl, halo$C_{1-10}$alkyl, —OR$^a$, —NR$^a$R$^a$, —NR$^a$C(O)R$^a$, —C(O)NR$^a$R$^a$, —C(O)R$^a$, —C(O)$_2$R$^a$, —SR$^a$, —S(O)R$^a$ and —S(O)$_2$R$^a$; wherein R$^a$ is independently, at each occurrence, selected from hydrogen and $C_{1-10}$alkyl;

or a salt or solvate thereof.

Aptly, a compound of the invention is for use as an imaging agent in fluorescent microscopy.

Compounds of the invention may be described as fluorophores.

Glutathione has the following structure:

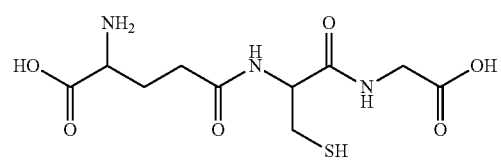 [SMILES: NC(CCC(=O)NC(CS)C(=O)NCC(=O)O)C(=O)O]

Aptly a glutathione derivative may have the following structure:

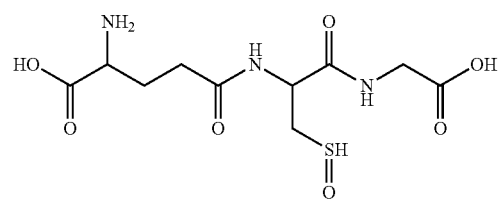

Aptly another glutathione derivative may have the following structure:

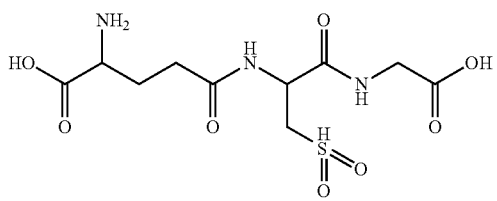

Aptly a further glutathione derivative may have the following structure:

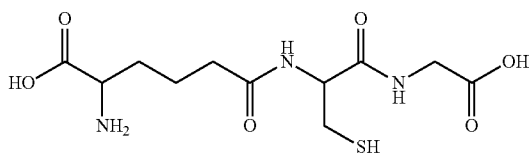 [SMILES: NC(CCCC(=O)NC(CS)C(=O)NCC(=O)O)C(=O)O]

In accordance with the invention, there is provided the use of a compound of the invention, for example a compound of formula (I), as an imaging agent in fluorescent microscopy.

In accordance with the invention, there is provided a process for the preparation of a compound of the invention, which process comprises reacting a compound of formula (II):

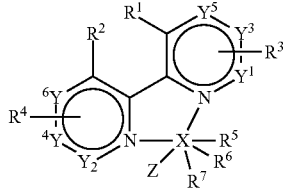

formula (II)

with a compound of formula (III):

 formula (III)

$R^8$—H wherein X, $Y^1$, $Y^2$, $Y^3$, $Y^4$, $Y^5$, $Y^6$, $R^1$, $R^2$, $R^3$, $R^4$, $R^5$, $R^6$, $R^7$ and $R^8$ are as defined herein; and Z is a leaving group.

In accordance with the invention, there is provided a product obtainable by a process of the invention, which process comprises reacting a compound of formula (II) with a compound of formula (III) as described herein.

BRIEF DESCRIPTION OF DRAWINGS

Certain embodiments of the present invention are described in more detail below with reference to the following drawings and/or figures.

DETAILED DESCRIPTION OF EMBODIMENTS OF THE INVENTION

Figure 1:
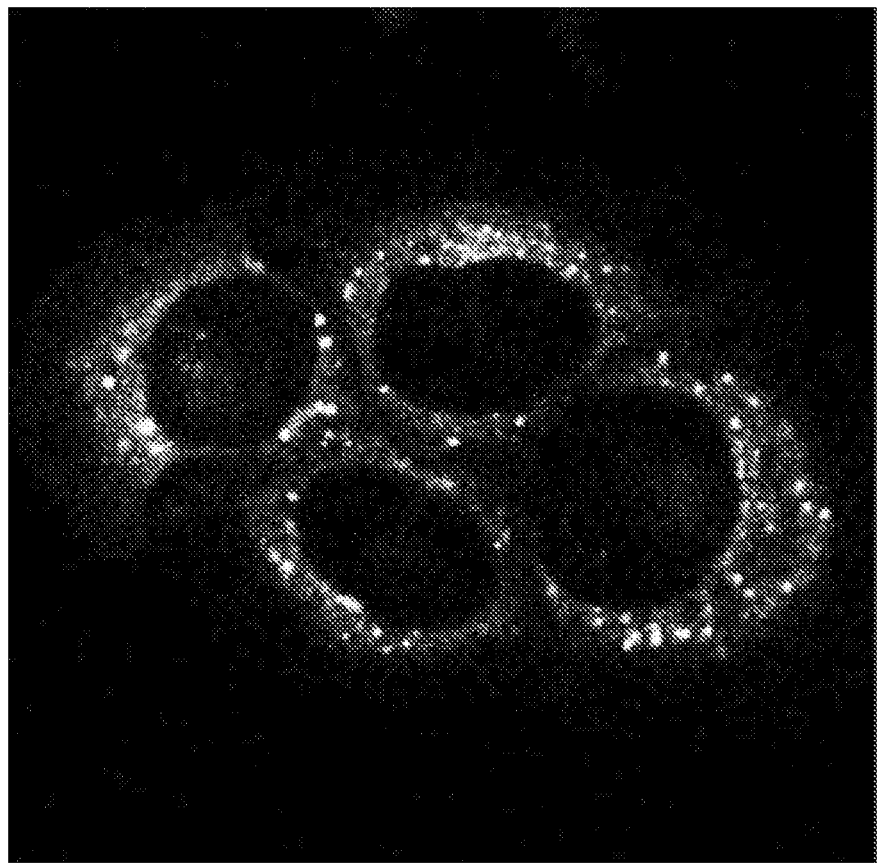
FIG. 1: Chemical structure of a compound of the invention (and the compound referred to in the figures for example as the platinum complex) and confocal micrograph of HaCaT cells after 10 minutes exposure to 25 μg/ml of the platinum complex (ex 405 nm, emission 505-740 nm). Staining shows a punctate pattern. A compound of the invention may be prepared as a salt, for example as a sodium salt as described herein, and is used as an imaging agent in a buffer solution.
Figure 1:
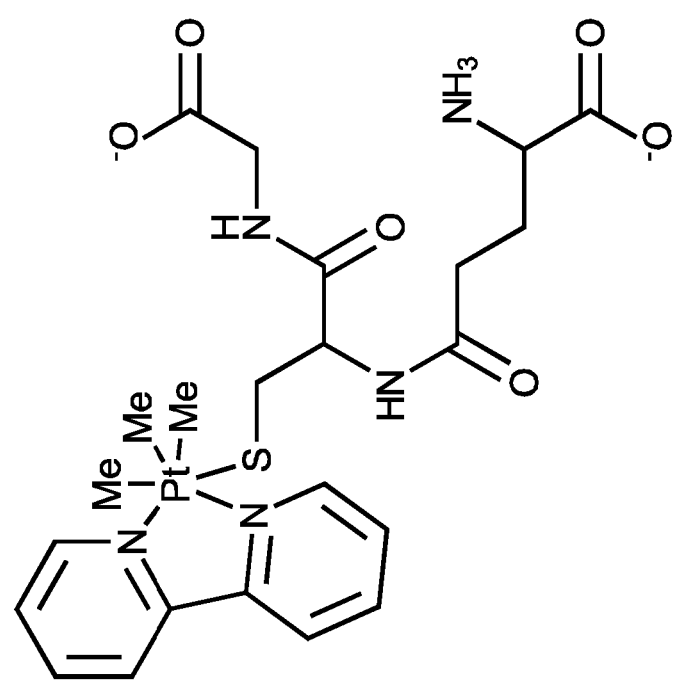

The practice of embodiments of the present invention will employ, unless otherwise indicated, conventional techniques of chemistry and molecular biology, in particular in the field of fluorescence microscopy, which are within the skill of those working in the art.

Most general chemistry techniques can be found in Comprehensive Heterocyclic Chemistry IF (Katritzky et al., 1996, published by Pergamon Press); Comprehensive Organic Functional Group Transformations (Katritzky et at., 1995, published by Pergamon Press); Comprehensive Organic Synthesis (Trost et al., 1991, published by Pergamon); Heterocyclic Chemistry (Joule et al. published by Chapman & Hall); Protective Groups in Organic Synthesis (Greene et al., 1999, published by Wiley-Interscience); and Protecting Groups (Kocienski et al., 1994).

Most general molecular biology techniques can be found in Sambrook et al, Molecular Cloning, A Laboratory Manual (2001) Cold Harbor-Laboratory Press, Cold Spring Harbor, N.Y. or Ausubel et al., Current Protocols in Molecular Biology (1990) published by John Wiley and Sons, N.Y.

Units, prefixes and symbols are denoted in their Système International d'Unités (SI) accepted form. Numeric ranges are inclusive of the numbers defining the range.

It will be appreciated that many of the terms and phases used within this specification will be known to the person skilled in the art. Unless defined otherwise, all technical and scientific terms used herein have the same meaning as commonly understood by one of ordinary skill in the art to which this disclosure belongs. For example, the Concise Dictionary of Biomedicine and Molecular Biology, Juo, Pei-Show, $2^{nd}$ ed., 2002, CRC Press; The Dictionary of Cell and Molecular Biology, $3^{rd}$ ed., Academic Press; and the Oxford University Press, provide a person skilled in the art with a general dictionary of many of the terms used in this disclosure. For chemical terms, the skilled person may refer to the International Union of Pure and Applied Chemistry (IUPAC).

Definitions provided herein are intended as embodiments of the invention separately and in any combination with any other definition, embodiments and/or claims provided herein.

Within this specification, the terms fluorescence, fluorescent and fluorophore are used without implying the specific nature of luminescence in any agent (fluorescence/hosphorescence) as this is convention in the field of biological imaging.

In this specification, the term 'alkyl' when used either alone or as a suffix or prefix or otherwise includes straight chain and branched chain saturated structures comprising carbon and hydrogen atoms.

The prefix $C_{m-n}$ (for example in $C_{m-n}$alkyl and other terms) where m and n are integers indicate the range of carbon atoms present in the group, for example $C_{1-4}$alkyl includes $C_1$alkyl (methyl), $C_2$alkyl (ethyl), $C_3$alkyl (propyl and isopropyl) and $C_4$alkyl (butyl, sec-butyl, isobutyl and tert-butyl).

The term '$C_{m-n}$alkoxy' comprises —O—$C_{m-n}$alkyl groups.

The term 'halo' includes fluoro, chloro, bromo and iodo.

The term 'aryl' refers to an aromatic hydrocarbon ring system having from 6 to 20 ring atoms. For example, the 'aryl' may be phenyl and/or naphthyl. The aryl group may be optionally substituted i.e. the aryl may be unsubstituted or substituted by one or more, for example 1 to 4 substituents. Specific substituents for each aryl group are independently selected from $C_{1-4}$alkyl, halo$C_{1-4}$alkyl, cyano, halo, —OR$^a$ and —NR$^a$R$^a$ wherein R$^a$ is a defined herein. Aryl groups may include non-aromatic carbocyclic portions.

The term 'heteroaryl' refers to an aromatic ring system having from 5 to 10 ring atoms wherein 1 to 4 of the ring atoms are heteroatoms independently selected from O, S and N. A heteroaryl may be independently selected from: 5-membered heteroaryl groups in which the heteroaromatic ring comprises 1 to 4 heteroatoms independently selected from O, S and N; 6-membered heteroaryl groups in which the heteroaromatic ring comprises 1 to 3 (for example 1 to 2) nitrogen atoms; 9-membered bicyclic heteroaryl groups in which the heteroaromatic system comprises 1 to 4 heteroatoms independently selected from O, S and N; 10-membered bicyclic heteroaryl groups in which the heteroaromatic system comprises 1 to 4 nitrogen atoms. Specifically, heteroaryl groups may be independently selected from: pyrrole, furan, thiophene, pyrazole, imidazole, oxazole, isoxazole, triazole, oxadiazole, thiadiazole, tetrazole; pyridine, pyridazine, pyrimidine, pyrazine, triazine, isoindole, benzofuran, isobenzofuran, benzothiophene, indazole, benzimidazole, benzoxazole, benzthiazole, benzisoxazole, purine, quinoline, isoquinoline, cinnoline, quinazoline, quinoxaline, pteridine, phthalazine, naphthyridine. Specifically, heteroaryl groups may be selected from: pyrrole, furan, thiophene, pyrazole, imidazole, oxazole, isoxazole, triazole, oxadiazole, thiodiazole, pyridine, pyridazine, pyrimidine and pyrazine. The heteroaryl group may be optionally substituted i.e. the heteroaryl may be unsubstituted or substituted by one or more, for example 1 to 4 substituents. Specific substituents for each heteroaryl group are independently selected from $C_{1-4}$alkyl, cyano, halo, —OR$^a$ and —NR$^a$R$^a$ wherein R$^a$ is a defined herein.

This specification makes use of composite terms to describe groups comprising more than one functionality. Such terms are to be understood according to the art.

Examples for some of the substituents and groups used herein include (and are not limited to):
$C_{1-4}$alkyl: methyl, ethyl, propyl, isopropyl;
$C_{1-10}$alkyl: $C_{1-4}$alkyl, hexyl, 4-methyloctyl, nonyl;
halo$C_{1-4}$alkyl: fluoromethyl, trifluoromethyl, 2-chloroethyl, 1,2-dichloroethyl, 2,2-dichloroethyl, 3-fluoropropyl;
halo$C_{1-10}$alkyl: halo$C_{1-4}$alkyl, fluorohexyl, 7-chlorononyl;
hydroxy$C_{1-4}$alkyl: hydroxymethyl, hydroxyethyl, 1-hydroxypropyl, 2-hydroxypropyl, 3-hydroxypropyl;
hydroxy$C_{1-10}$alkyl: hydroxy$C_{1-4}$alkyl, 2-hydroxypentyl, 7-hydroxyheptyl; methoxy, ethoxy, propoxy;
$C_{1-10}$alkoxy: $C_{1-4}$alkoxy, hexyloxy, 2,5-dimethyl-6-octyloxy;
$C_{1-4}$alkoxy$C_{1-4}$alkyl: methoxymethyl, ethoxymethyl, methoxyethyl;
$C_{1-10}$alkoxy$C_{1-10}$alkyl, 6-methoxyhexyl;
nitro$C_{1-4}$alkyl: nitromethyl, nitroethyl;
nitro$C_{1-10}$alkyl: nitro$C_{1-4}$alkyl, 3-ethyl-6-nitrohexyl, nitrodecyl;
$C_{1-4}$alkylamino: methylamino, ethylamino;
$C_{1-10}$alkylamino: $C_{1-4}$alkylamino, pentylamino;
bis($C_{1-4}$alkyl)amino: dimethylamino, ethyl(methyl)amino;
bis($C_{1-10}$alkyl)amino: bis($C_{1-4}$alkyl)amino, isopropyl(pentyl)amino;
amino$C_{1-4}$alkyl: aminomethyl, aminoethyl, 2-aminoethyl;
amino$C_{1-10}$alkyl: amino$C_{1-4}$alkyl, aminodecyl;
$C_{1-4}$alkylamino$C_{1-4}$alkyl: methylaminomethyl, methylaminoethyl;
$C_{1-10}$alkylamino$C_{1-10}$alkyl: $C_{1-4}$alkylamino$C_{1-4}$alkyl, 8-methylaminononyl
bis($C_{1-4}$alkyl)amino$C_{1-4}$alkyl: dimethylaminomethyl, diethylaminomethyl, methyl(ethyl)aminoethyl;
bis($C_{1-10}$alkyl)amino$C_{1-10}$alkyl, 6-ethyl(propyl)aminohexyl With this specification bpy represents 2,2'-bipyridine.

Where optional substituents are present, for example in optionally substituted $C_{1-10}$alkyl, optionally substituted aryl, optionally substituted heteroaryl or optionally substituted ring system(s), the optional substituents may be chosen from 1, 2, 3 or 4 (for example 1, 2 or 3, for example 1 or 2) substituents. It is to be understood that this definition includes all substituents being chosen from one of the specified groups i.e. all substituents being the same, or the substituents being chosen from two or more of the specified groups i.e. the substituents not being the same. Examples of optional substituents include halo, nitro, cyano, $C_{1-4}$alkyl, halo$C_{1-4}$alkyl, —OR$^a$, —NR$^a$R$^a$, —NR$^3$C(O)R$^a$, —C(O)NR$^a$R$^a$, —C(O)R$^a$, —C(O)$_2$R$^a$, —SR$^a$, —S(O)R$^a$ and —S(O)$_2$R$^a$; wherein R$^3$ is independently, at each occurrence, selected from hydrogen and $C_{1-10}$alkyl. Aptly, R$^a$ is independently, at each occurrence, selected from hydrogen and $C_{1-4}$alkyl.

Within the present invention, it is to be understood that a compound of the invention may exhibit the phenomenon of tautomerisation and that the formulae drawings within this specification can represent only one of the possible tautomeric forms. It is to be understood that the invention encompasses all tautomeric forms and is not to be limited merely to any one of the tautomeric forms used within the formulae drawings.

It is also to be understood that certain compounds of the invention may exist as salts or as solvated as well as unsolvated forms and that the invention encompasses all such forms.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Further details of certain embodiments are provided herein.

Particular values of X, $Y^1$, $Y^2$, $Y^3$, $Y^4$, $Y^5$, $Y^6$, $R^1$, $R^2$, $R^3$, $R^4$, $R^5$, $R^6$, $R^7$ and $R^8$ are as follows.

These values are intended as embodiments of the invention and may be used where appropriate with any of the definitions, embodiments or claims provided herein.

In one embodiment, X is platinum. In another embodiment, X is rhenium.

In one embodiment, $Y^1$ is —CH—.
In one embodiment, $Y^1$ is —N—.
In one embodiment, $Y^2$, $Y^4$ and $Y^6$ are each —CH—.
In one embodiment, $Y^1$, $Y^3$ and $Y^5$ are each —CH—.
In one embodiment, $Y^3$ is —CH— and $Y^5$ is —N—.
In one embodiment, $Y^3$ is absent and $Y^5$ is —NR$^9$—.
In one embodiment, $Y^1$, $Y^2$, $Y^3$, $Y^4$, $Y^5$ and $Y^6$ are each —CH—.
In one embodiment, $Y^1$, $Y^2$, $Y^3$, $Y^4$ and $Y^6$ are each —CH— and $Y^5$ is —N—.

In one embodiment, $R^1$ and $R^2$ are independently hydrogen or a substituent selected from $C_{1-4}$alkyl, halo, halo$C_{1-4}$alkyl, hydroxy, hydroxy$C_{1-4}$alkyl, $C_{1-4}$alkoxy, $C_{1-4}$alkoxy$C_{1-4}$alkyl, nitro, nitro$C_{1-4}$alkyl, amino, $C_{1-4}$alkylamino, bis($C_{1-4}$alkyl)amino, amino$C_{1-4}$alkyl, $C_{1-4}$alkylamino$C_{1-4}$alkyl, bis($C_{1-4}$alkyl)amino$C_{1-4}$alkyl, optionally substituted aryl and optionally substituted heteroaryl; wherein when any of the aforementioned aryl and/or heteroaryl groups are optionally substituted, the optional substituents, where chemically possible, are selected from 1 to 4 substituents which are independently, at each occurrence, selected from halo, nitro, cyano, $C_{1-4}$alkyl, halo$C_{1-4}$alkyl, —OR$^a$, —NR$^a$R$^a$, —NR$^a$C(O)R$^a$, —C(O)NR$^a$R$^a$, —C(O)R$^a$, —C(O)$_2$R$^a$, —SR$^a$, —S(O)R$^a$ and —S(O)$_2$R$^a$; wherein R$^a$ is independently, at each occurrence, selected from hydrogen and $C_{1-4}$alkyl.

In one embodiment, $R^1$ and $R^2$ are independently a substituent selected from optionally substituted $C_{1-4}$alkyl, optionally substituted aryl and optionally substituted heteroaryl.

In one embodiment, $R^1$ and $R^2$ are independently a substituent selected from $C_{1-4}$alkyl, halo, halo$C_{1-4}$alkyl, hydroxy, hydroxy$C_{1-4}$alkyl, $C_{1-4}$alkoxy, $C_{1-4}$alkoxy$C_{1-4}$alkyl, nitro, nitro$C_{1-4}$alkyl, amino, $C_{1-4}$alkylamino, bis($C_{1-4}$alkyl)amino, amino$C_{1-4}$alkyl, $C_{1-4}$alkylamino$C_{1-4}$alkyl and bis($C_{1-4}$alkyl)amino$C_{1-4}$alkyl.

In one embodiment, $R^1$ is hydrogen.
In one embodiment, $R^2$ is hydrogen.
In one embodiment $R^1$ and $R^2$ are both hydrogen.

In one embodiment, $R^1$ and $R^2$ together with the atoms to which they are attached together form an optionally substituted ring system. In one embodiment, the ring system is optionally substituted by 1 or 2 substituents independently selected from $R^{11}$ wherein $R^{11}$ at each occurrence, is selected from hydrogen, optionally substituted $C_{1-4}$alkyl, optionally substituted aryl and optionally substituted heteroaryl.

In one embodiment, the substructure formed when $R^1$ and $R^2$ together with the atoms to which they are attached form an optionally substituted 6 membered monocyclic ring, is of subformula (IA) wherein ---- represents the point of attachment to X and wherein $R^{11}$ is selected from hydrogen, optionally substituted $C_{1-4}$alkyl, optionally substituted aryl and optionally substituted heteroaryl.

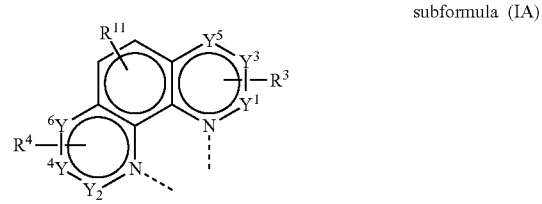

subformula (IA)

In one embodiment, $R^1$ and $R^2$ together with the atoms to which they are attached form an optionally substituted 6 membered monocyclic ring. In one embodiment, the substructure formed when $R^1$ and $R^2$ together with the atoms to which they are attached form a 6 membered monocyclic ring, is of subformula (IB) wherein ---- represents the point of attachment to X and wherein $R^{11}$ is selected from hydrogen, optionally substituted $C_{1-4}$alkyl, optionally substituted aryl and optionally substituted heteroaryl.

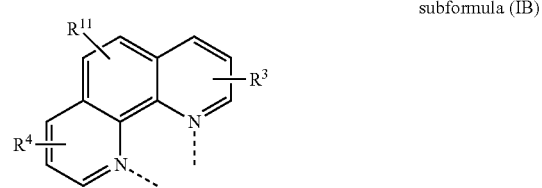

subformula (IB)

In one embodiment, $R^1$ and $R^2$ together with the atoms to which they are attached form an optionally substituted tricyclic ring system. In one embodiment, the substructure formed when $R^1$ and $R^2$ together with the atoms to which they are attached form a tricyclic ring system is of subformula (IC) wherein ---- represents the point of attachment to X and wherein $R^{11}$ is selected from hydrogen, optionally substituted $C_{1-4}$alkyl, optionally substituted aryl and optionally substituted heteroaryl.

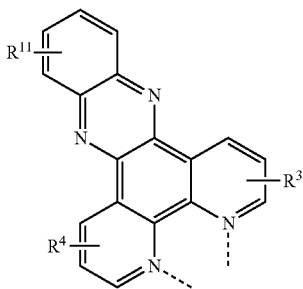

subformula (IC)

In one embodiment, $R^1$ and $R^2$ together with the atoms to which they are attached form an optionally substituted 6 membered monocyclic ring. In one embodiment, the substructure formed when $R^1$ and $R^2$ together with the atoms to which they are attached form a 6 membered monocyclic ring, is of subformula (ID) wherein ---- represents the point of attachment to X and wherein $R^{11}$ is selected from hydrogen, optionally substituted $C_{1-4}$alkyl, optionally substituted aryl and optionally substituted heteroaryl:

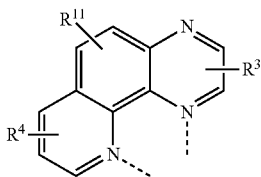

subformula (ID)

In one embodiment, the substructure formed by $R^1$ and $R^2$ together with the atoms to which they are attached, is of subformula (IE) wherein ---- represents the point of attachment to X:

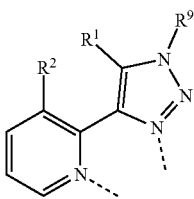

subformula (IE)

In one embodiment, $R^{11}$ is hydrogen.

In one embodiment, $R^3$ and $R^4$ are independently hydrogen or a substituent selected from $C_{1-4}$alkyl, halo, halo$C_{1-4}$alkyl, hydroxy, hydroxy$C_{1-4}$alkyl, $C_{1-4}$alkoxy, $C_{1-4}$alkoxy$C_{1-4}$alkyl, nitro, nitro$C_{1-4}$alkyl, amino, $C_{1-4}$alkylamino, bis($C_{1-4}$alkyl)amino, amino$C_{1-4}$alkyl, $C_{1-4}$alkylamino$C_{1-4}$alkyl, bis($C_{1-4}$alkyl)amino$C_{1-4}$alkyl, optionally substituted aryl and optionally substituted heteroaryl; wherein when any of the aforementioned aryl and/or heteroaryl groups are optionally substituted, the optional substituents, where chemically possible, are selected from 1 to 4 substituents which are independently, at each occurrence, selected from halo, nitro, cyano, halo$C_{1-4}$alkyl, —$OR^a$, —$NR^aR^a$, —$NR^aC(O)R^a$, —$C(O)NR^aR^a$, —$C(O)R^a$, —$C(O)_2R^a$, —$SR^a$, —$S(O)R^a$ and —$S(O)_2R^a$; wherein $R^a$ is independently, at each occurrence, selected from hydrogen and $C_{1-4}$alkyl.

In one embodiment, $R^3$ and $R^4$ are independently a substituent selected from optionally substituted $C_{1-4}$alkyl, optionally substituted aryl and optionally substituted heteroaryl.

In one embodiment, $R^3$ and $R^4$ are independently a substituent selected from $C_{1-4}$alkyl, halo, halo$C_{1-4}$alkyl, hydroxy, hydroxy$C_{1-4}$alkyl, $C_{1-4}$alkoxy, $C_{1-4}$alkoxy$C_{1-4}$alkyl, nitro, nitro$C_{1-4}$alkyl, amino, $C_{1-4}$alkylamino, bis($C_{1-4}$alkyl)amino, amino$C_{1-4}$alkyl, $C_{1-4}$alkylamino$C_{1-4}$alkyl and bis($C_{1-4}$alkyl)amino$C_{1-4}$alkyl.

In one embodiment, $R^3$ is hydrogen.

In one embodiment, $R^4$ is hydrogen.

In one embodiment $R^3$ and $R^4$ are both hydrogen.

In one embodiment, $R^5$, $R^6$ and $R^7$ are each independently selected from optionally substituted $C_{1-4}$alkyl, optionally substituted aryl, optionally substituted heteroaryl and —CO.

In one embodiment, $R^5$, $R^6$ and $R^7$ are each independently selected from $C_{1-4}$alkyl and —CO.

In one embodiment, $R^5$ is methyl. In one embodiment, $R^5$ is —CO.

In one embodiment, $R^6$ is methyl. In one embodiment, $R^6$ is —CO.

In one embodiment, $R^7$ is methyl. In one embodiment, $R^7$ is —CO.

In one embodiment, $R^8$ is glutathione or a derivative thereof linked to X through sulphur.

In one embodiment glutathione is L-glutathione.

In one embodiment, a glutathione derivative is a glutathione derived ester or amide. In one embodiment, a glutathione derivative is an oxidised sulphur derivative, for example derived by oxidising sulphur (S) to S(O) and/or $S(O)_2$.

In one embodiment, $R^9$ and $R^{19}$ are each independently selected from hydrogen and $C_{1-4}$alkyl.

In one embodiment, there is provided a compound of formula (IV):

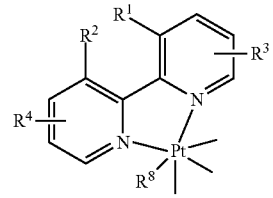

formula (IV)

wherein $R^1$, $R^2$, $R^3$, $R^4$ and $R^8$ are each independently as defined herein.

In one embodiment, there is provided a compound of formula (V):

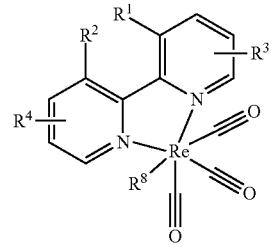

formula (V)

wherein $R^1$, $R^2$, $R^3$, $R^4$ and $R^8$ are each independently as defined herein.

In one embodiment, there is provided a compound of formula (VI):

formula (VI)

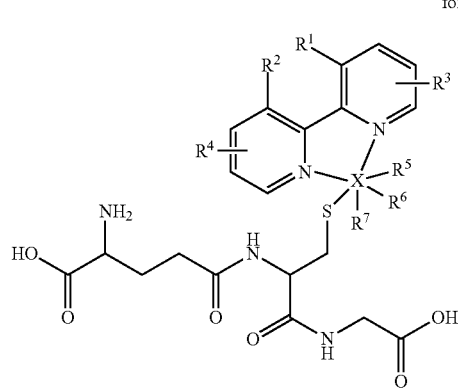

wherein $R^1$, $R^2$, $R^3$, $R^4$, $R^5$, $R^6$ and $R^7$ are each independently as defined herein.

In one embodiment, there is provided a compound of formula (VIA):

formula (VIA)

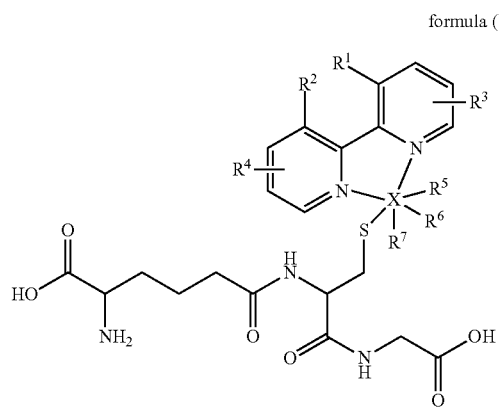

wherein $R^1$, $R^2$, $R^3$, $R^4$, $R^5$, $R^6$ and $R^7$ are each independently as defined herein. In one embodiment, there is provided a compound of formula (VII):

formula (VII)

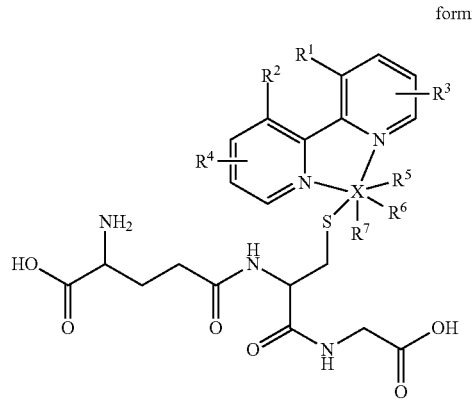

wherein $R^1$, $R^2$, $R^3$ and $R^4$ are each independently as defined herein

In one embodiment, there is provided a compound of formula (VIIA):

formula (VIIA)

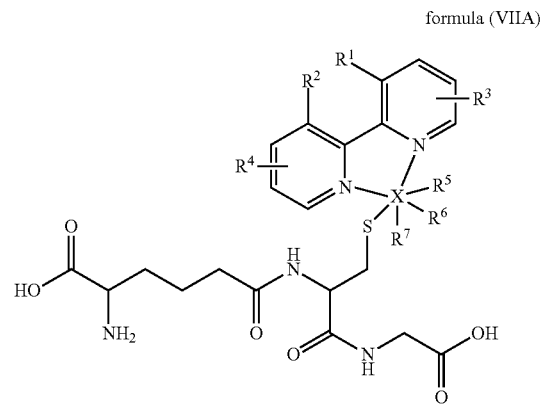

wherein $R^1$, $R^2$, $R^3$ and $R^4$ are each independently as defined herein.

In one embodiment, there is provided a compound of formula (VIII):

formula (VIII)

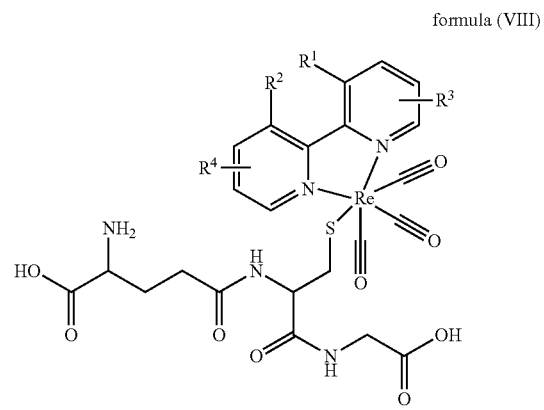

wherein $R^1$, $R^2$, $R^3$ and $R^4$ are each independently as defined herein.

In one embodiment, there is provided a compound of formula (VIIIA):

formula (VIIIA)

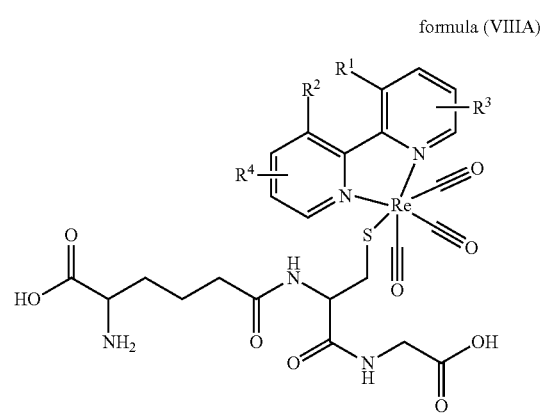

wherein $R^1$, $R^2$, $R^3$ and $R^4$ are each independently as defined herein.

A particular compound of the invention is compound A:

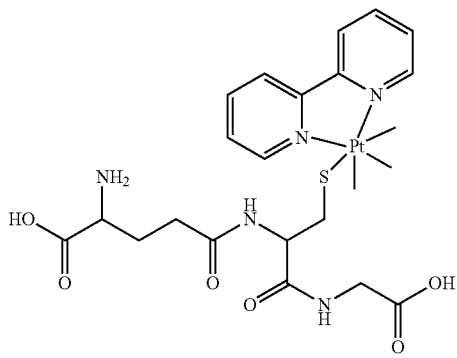

A particular compound of the invention is compound A':

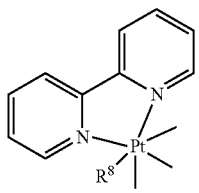

wherein $R^8$ is glutathione linked to Pt through sulphur, for example L-glutathione; or a salt or solvate thereof.

A particular compound of the invention is compound A":

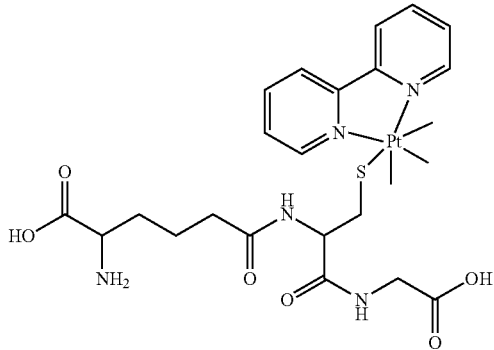

A particular compound of the invention is compound B:

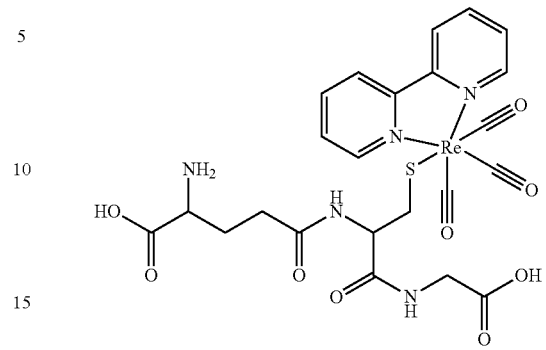

A particular compound of the invention is compound B':

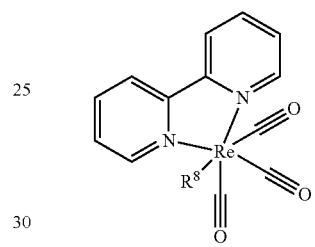

wherein $R^8$ is glutathione linked to Re through sulphur, for example L-glutathione; or a salt or solvate thereof.

A particular compound of the invention is compound B":

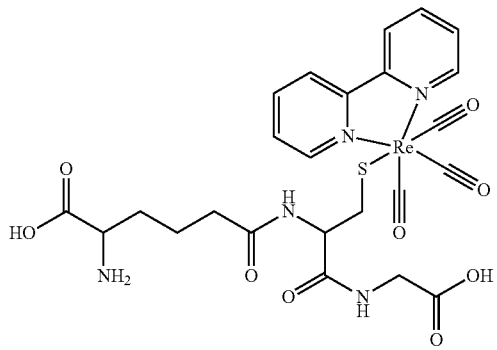

Compounds of the invention may be prepared by reacting a compound of formula (II):

formula (II)

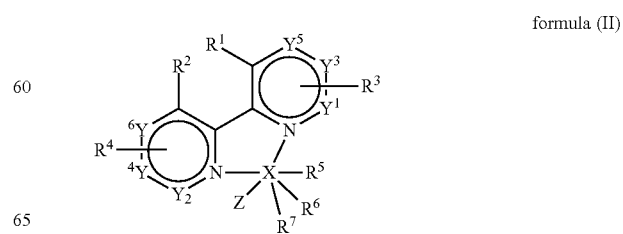

with a compound of formula (III):

R$^8$—H                                   formula (VIII)

wherein X, Y$^1$, Y$^2$, Y$^3$, Y$^4$, Y$^5$, Y$^6$, R$^1$, R$^2$, R$^3$, R$^4$, R$^5$, R$^6$, R$^7$ and R$^8$ are as defined herein; and Z is a leaving group, for example halo (for example iodo or chloro) or triflate in a suitable solvent such as acetonitrile or tetrahydrofuran, under basic conditions such as with the use of sodium or potassium hydroxide or alkoxide(s).

A compound of formula (II) may be prepared according to the art, particularly as described in Steel et al (2015), Platinum trimethyl bipyridyl thiolates—new, tunable, red- to near IR emitting luminophores for bioimaging applications, *Chem. Commun.*, Vol. 51, 11441 and Aomoroso et al, (2010), Uptake and Localisation of Rhenium fac-Tricarbonyl Polypyridyls in Fluorescent Cell Imaging Experiments, Establishing The Ground-Rules For Fluorescent Cell Imaging With Rhenium fac-Tricarbonyl Polypyridyl Complexes, *Org. Blomoi. Chem.* Vol. 8, 3888.

EXAMPLE 1

PtMe$_3$bpyl (20 mg, 3.8×10$^{-5}$ mol) was dissolved in MeCN (5 ml) and to this solution was added a solution of glutathione (14 mg, 4.6×10$^{-5}$ mol) in water (5 ml) which had been adjusted to pH 9 by the addition of NaOH (1M, eq.). The mixture was stirred at room temperature for 16 hours and evaporated to dryness before purification by ion exchange chromatography (Amberlite IRA-400) and evaporated to dryness to give PtMe$_3$bpy-S-glutathione (55%) as a yellow solid.

PtMe$_3$bpyl was prepared according to Steel et al. (2015), Platinum trimethyl bipyridyl thiolates—new, tunable, red- to near IR emitting luminophores for bioimaging applications, *Chem. Commun.*, Vol. 51, 11441

This material may also be conveniently prepared in situ without further purification for immediate use by the following procedure:

PtMe$_3$bpyl (2.00 mg, 3.8×10$^{-6}$ mol) was dissolved in DMSO (0.2 ml) and to this solution was added a solution of glutathione (1.15 mg, 3.8×10$^{-6}$ mol) in water (0.2 ml) which had been adjusted to pH 9 by the addition of NaOH (1M, aq.). The mixture was incubated at 40° C. for 30 minutes and then used directly.

EXAMPLE 2

Re(CO)$_3$bpyBr (25 mg, 5.1×10$^{-5}$ mol) was dissolved in MeCN (5 ml) and to this solution was added a solution of glutathione (16 mg, 5.2×10$^{-5}$ mol) in water (5 ml) which had been adjusted to pH 9 by the addition of NaOH (1M, aq.). The reaction mixture was heated at 75° C. for 5 hours during which time the initial yellow colour turned to a deep red. The solution was evaporated to dryness and redissolved in boiling water (1 ml) with the addition of methanol (5 drops) then allowed to cool to room temperature.

Re(CO)$_3$bpyBr was prepared according to Aomoroso et al., (2010), Uptake and Localisation of Rhenium fac-Tricarbonyl Polypyridyls in Fluorescent Cell Imaging Experiments, Establishing The Ground-Rules For Fluorescent Cell Imaging With Rhenium fac-Tricarbonyl Polypyridyl Complexes, *Org. Biomol, Chem.* Vol, 8, 3888.

EXAMPLE 3

Demonstration of Peroxisomal Selectivity

Figure 2:
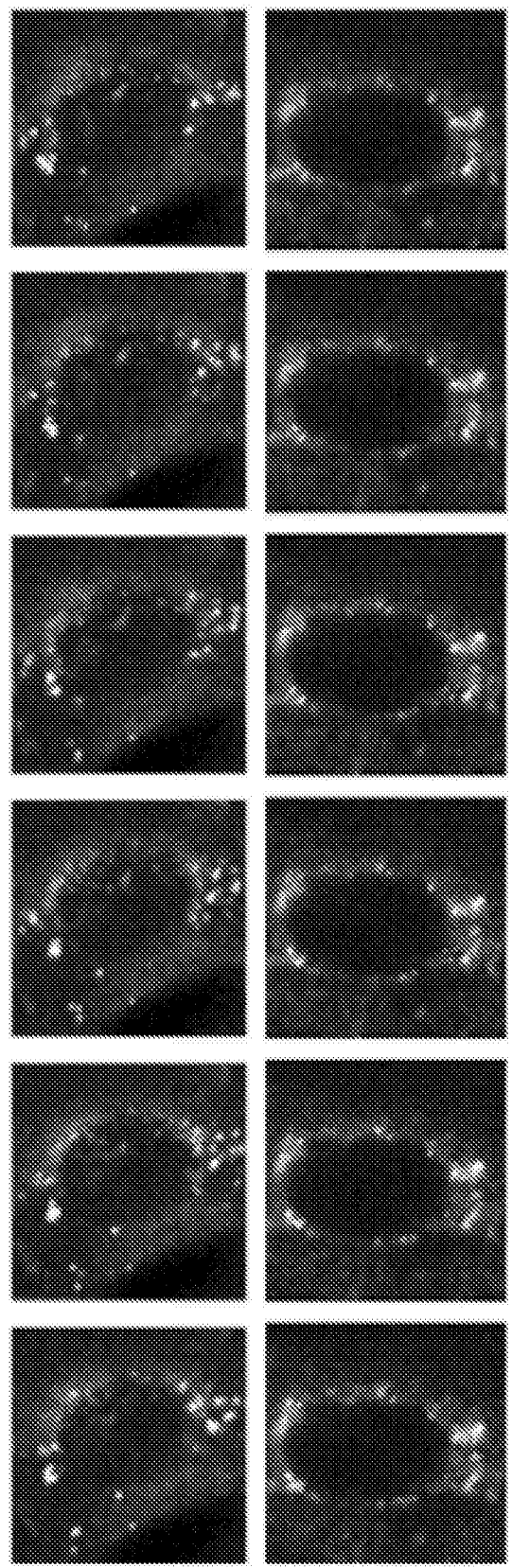
FIG. 2: Time-lapse fluorescence imaging in HaCaT cells that have been treated with nocodazole (bottom row) or left untreated (top row, sequential images taken at 30 s intervals). The platinum complex labelled components are only motile in the absence of the microtubule depolymerising agent, nocodazole.
Figure 3:
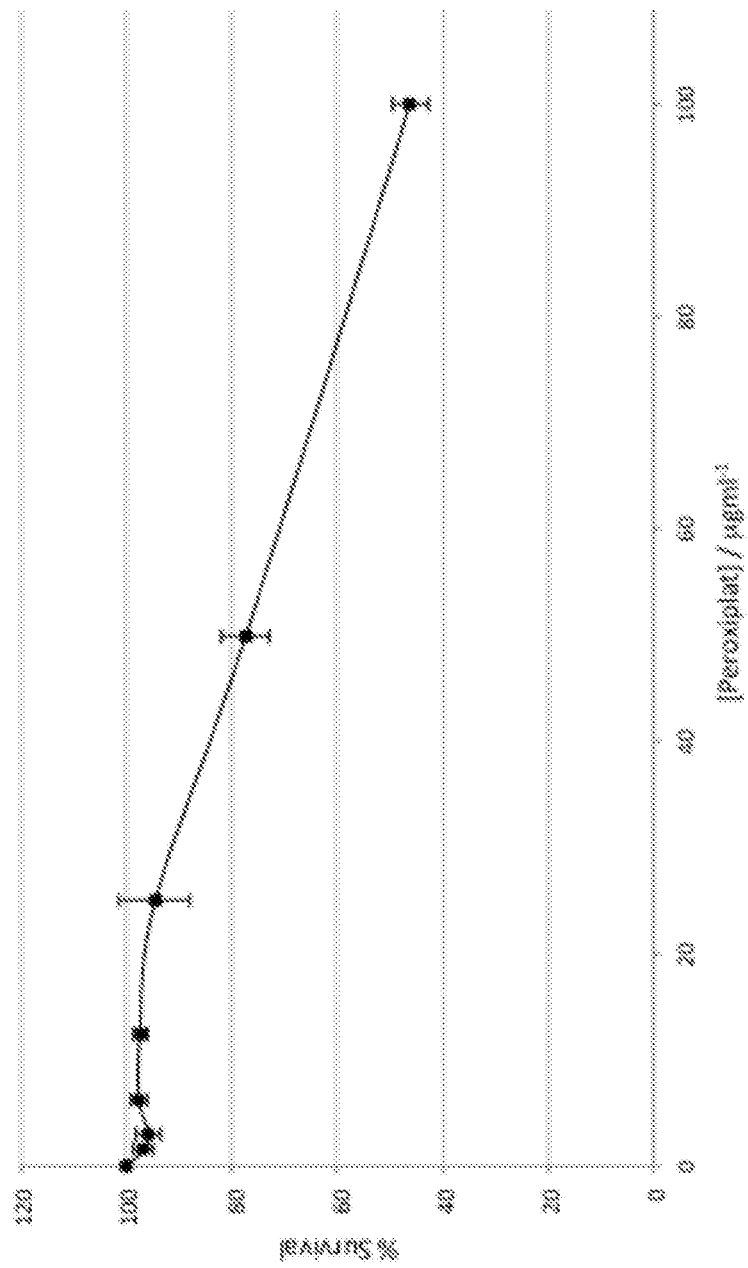
FIG. 3: XTT assay of HaCaT proliferation when incubated with the compound of figure IA at the indicated concentrations for 48 hours.
Figure 4:
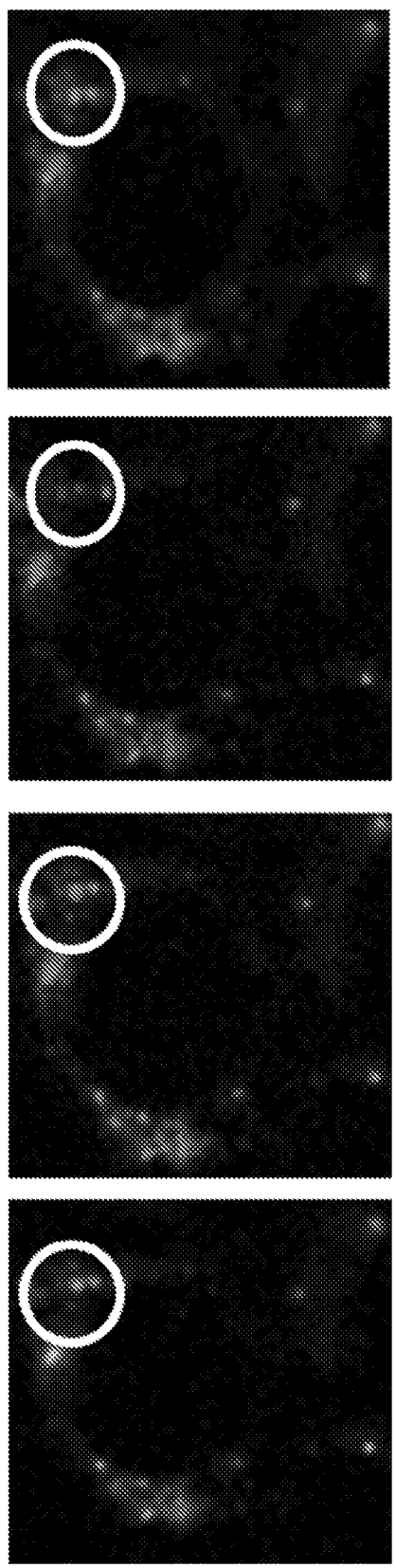
FIG. 4: Co-localisation experiment with Clontech pDsRed2-Peroxi Vector. Co-localisation demonstrated by loss of DsRed signal upon photo-bleaching the circled area at 514 nm (DsRed absorption maximum) while platinum complex emission is retained (excited at 405 nm). Fluorescence micrographs of co-localisation experiment i) Excited at 405 nm pre-photo-bleaching; ii) excited at 514 nm pre photo-bleaching iii) excited at 514 nm post photo-bleaching; iv) Excited at 405 nm post photo-bleaching.

HaCaT cells were grown on glass coverslips under the same conditions as in described in Steel 2015 referred to herein. The coverslips were washed briefly in PBS and then incubated in PBS containing compound A at 125 µg/ml for 10 minutes at 4° C. The coverslips were then washed in PBS and mounted by inversion on a glass slide. Images were captured on a Zeiss LSM 850 Meta laser scanning confocal microscope. The complex was readily taken up by cells (FIG. 1) and showed a punctate staining pattern, characteristic of peroxisomes. Further evidence that compound A is peroxisomally-located was obtained by analysing the motility of the stained compartments with and without the presence of microtubule-depolymerising levels of nocodazole (FIG. 2). The compartments showed microtubule-dependent motility, as has been previously demonstrated for peroxisomes. The low toxicity of the platinum complex was demonstrated in an XTT assay (FIG. 3). Finally, co-localisation with Clontech pDsRed2-Peroxi Vector was demonstrated by photo-bleaching the Clontech pDsRed2-Peroxi Vector emission and demonstrating that platinum complex emission was retained in the same cellular compartments (overlapping excitation prevented conventional co-localisation techniques) (FIG. 4).

The invention claimed is:

1. A compound of formula (I):

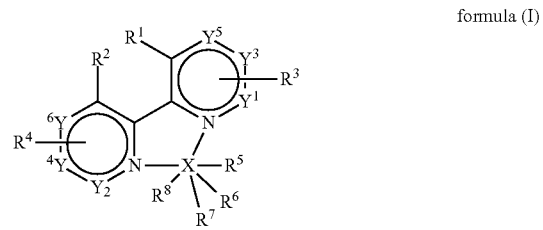

formula (I)

wherein:
X is selected from platinum and rhenium;
Y$^1$ is selected from —CH— and —N—;
Y$^3$ is —CH— or Y$^3$ is absent provided that when Y$^3$ is —CH—, Y$^5$ is selected from —CH— and —N—, and that when Y$^3$ is absent, Y$^5$ is —NR$^9$—;
Y$^2$ is selected from —CH— and —N—;
Y$^4$ is —CH— or Y$^4$ is absent provided that when Y$^4$ is —CH—, Y$^6$ is selected from —CH— and —N—, and that when Y$^4$ is absent, Y$^6$ is —NR$^{10}$—;
R$^1$ and R$^2$ are independently hydrogen or a substituent selected from C$_{1-10}$alkyl, halo, haloC$_{1-10}$alkyl, hydroxy, hydroxyC$_{1-10}$alkyl, C$_{1-10}$alkoxy, C$_{1-10}$alkoxyC$_{1-10}$alkyl, nitro, nitroC$_{1-10}$alkyl, amino, C$_{1-10}$alkylamino, bis(C$_{1-10}$alkyl)amino, aminoC$_{1-10}$alkyl, C$_{1-10}$alkylaminoC$_{1-10}$alkyl, bis(C$_{1-10}$alkyl)aminoC$_{1-10}$alkyl, aryl and heteroaryl wherein any alkyl, aryl and/or heteroaryl portion of a substituent is independently optionally substituted;
or R$^1$ and R$^2$ together with the atoms to which they are attached together form an optionally substituted ring system;
R$^3$ and R$^4$ are independently hydrogen or a substituent selected from C$_{1-10}$alkyl, halo, haloC$_{1-10}$alkyl, hydroxy, hydroxyC$_{1-10}$alkyl, C$_{1-10}$alkoxy, C$_{1-10}$alkoxyC$_{1-10}$alkyl, nitro, nitroC$_{1-10}$alkyl, amino, C$_{1-10}$alkylamino, bis(C$_{1-10}$alkyl)amino, aminoC$_{1-10}$alkyl, C$_{1-10}$alkylaminoC$_{1-10}$alkyl, bis(C$_{1-10}$alkyl)aminoC$_{1-10}$alkyl, aryl and heteroaryl wherein any alkyl, aryl and/or heteroaryl portion of a substituent is independently optionally substituted;

$R^5$, $R^6$ and $R^7$ are each independently selected from optionally substituted $C_{1-10}$alkyl, optionally substituted aryl, optionally substituted heteroaryl and —CO;

$R^8$ is glutathione or a derivative thereof linked to X through sulfur, wherein the derivative is selected from a glutathione derived ester, a glutathione derived amide and glutathione oxidized at S to S(O) or S(O)$_2$;

$R^9$ and $R^{10}$ are each independently selected from hydrogen and $C_{1-10}$alkyl; and wherein when any of the aforementioned alkyl, aryl and/or heteroaryl groups and/or ring systems are optionally substituted, the optional substituents, where chemically possible, are selected from 1 to 4 substituents which are independently, at each occurrence, selected from halo, nitro, cyano, $C_{1-4}$alkyl, halo$C_{1-4}$alkyl, —OR$^a$, —NR$^a$R$^a$, —NR$^a$C(O)R$^a$, —C(O)NR$^a$R$^a$, —C(O)R$^a$, —C(O)$_2$R$^a$, —SR$^a$, —S(O)R$^a$ and —S(O)$_2$R$^a$; wherein R$^a$ is independently, at each occurrence, selected from hydrogen and $C_{1-10}$alkyl;

or a salt or solvate thereof.

2. The compound according to claim 1 wherein $R^1$ is hydrogen and $R^2$ is hydrogen; or a salt or solvate thereof.

3. The compound according to claim 1 wherein $R^1$ and $R^1$ together with the atoms to which they are attached form an optionally substituted 6 membered monocyclic ring such that the substructure formed is of subformula (IB) wherein ---- represents the point of attachment to X and wherein $R^{11}$ is selected from hydrogen, optionally substituted $C_{1-4}$alkyl, optionally substituted aryl and optionally substituted heteroaryl; or a salt or solvate thereof;

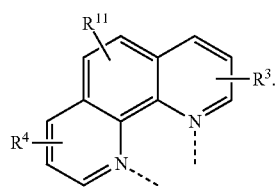

subformula (IB)

4. The compound according to claim 1 wherein $R^1$ and $R^2$ together with the atoms to which they are attached form an optionally substituted tricyclic ring system such that the substructure formed is of subformula (IC) wherein ---- represents the point of attachment to X and wherein $R^{11}$ is selected from hydrogen, optionally substituted $C_{1-4}$alkyl, optionally substituted aryl and optionally substituted heteroaryl; or a salt or solvate thereof

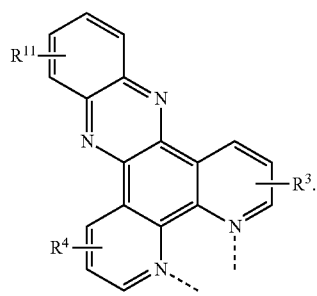

subformula (IC)

5. The compound according to claim 1 wherein $R^1$ and $R^2$ together with the atoms to which they are attached form an optionally substituted 6 membered monocyclic ring such that the substructure formed is of subformula (ID) wherein ---- represents the point of attachment to X and wherein $R^{11}$ is selected from hydrogen, optionally substituted $C_{1-4}$alkyl, optionally substituted aryl and optionally substituted heteroaryl; or a salt or solvate thereof

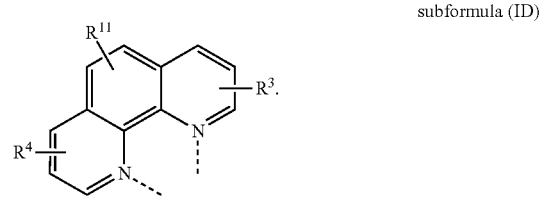

subformula (ID)

6. The compound according to claim 1 wherein $R^1$ and $R^2$ together with the atoms to which they are attached form a substructure that is of subformula (IE) wherein ---- represents the point of attachment to X; or a salt or solvate thereof

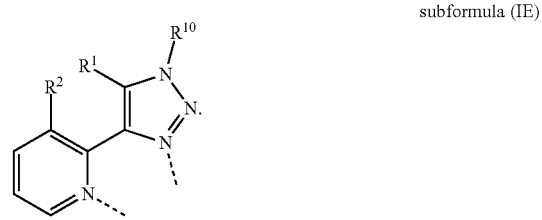

subformula (IE)

7. The compound according to claim 1 wherein $R^3$ is hydrogen and $R^4$ is hydrogen; or a salt or solvate thereof.

8. The compound according to claim 1 wherein X is platinum; or a salt or solvate thereof.

9. The compound according to claim 8 wherein $R^5$, $R^6$ and $R^7$ are each independently methyl; or a salt or solvate thereof.

10. The compound according to claim 1 wherein X is rhenium; or a salt or solvate thereof.

11. The compound according to claim 10 wherein $R^5$, $R^6$ and $R^7$ are each independently —CO; or a salt or solvate thereof.

12. The compound according to claim 1 wherein glutathione is L-glutathione; or a salt or solvate thereof.

13. A method comprising contacting a compound of claim 1 with a cell and imaging a subcellular structure of the cell.

14. A process for the preparation of a compound of Formula (I) according to claim 1, which process comprises reacting a compound of formula (II):

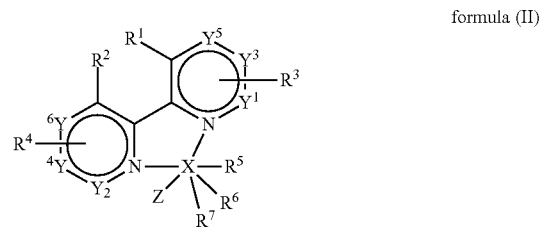

formula (II)

with a compound of formula (III):

R⁸—H  formula (III)

wherein X, Y¹, Y², Y³, Y⁴, Y⁵, Y⁶, R¹, R², R³, R⁴, R⁵, R⁶, R⁷ and R⁸ are as defined according to claim 1; and Z is a leaving group.

15. The compound according to claim 1 wherein R¹ and R² together with the atoms to which they are attached form an optionally substituted 6 membered monocyclic ring such that the substructure formed is of subformula (IB) wherein ---- represents the point of attachment to X and wherein R¹¹ is selected from hydrogen, optionally substituted C₁₋₄alkyl, optionally substituted aryl and optionally substituted heteroaryl; or a salt or solvate thereof

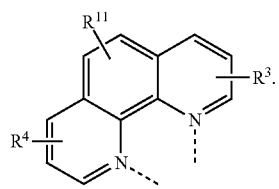

subformula (IB)

16. The compound according to claim 1 wherein R¹ and R² together with the atoms to which they are attached form an optionally substituted tricyclic ring system such that the substructure formed is of subformula (IC) wherein ---- represents the point of attachment to X and wherein R¹¹ is selected from hydrogen, optionally substituted C₁₋₄alkyl, optionally substituted aryl and optionally substituted heteroaryl; or a salt or solvate thereof

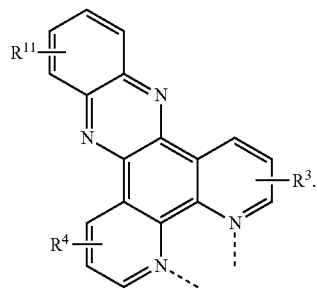

subformula (IC)

17. The compound according to claim 1 wherein R¹ and R² together with the atoms to which they are attached form an optionally substituted 6 membered monocyclic ring such that the substructure formed in is of subformula (ID) wherein ---- represents the point of attachment to X and wherein R¹¹ is selected from hydrogen, optionally substituted C₁₋₄alkyl, optionally substituted aryl and optionally substituted heteroaryl; or a salt or solvate thereof

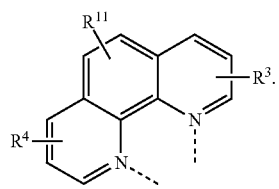

subformula (ID)

18. The compound according to claim 1 wherein R¹ and R² together with the atoms to which they are attached form a substructure that is of subformula (IE) wherein ---- represents the point of attachment to X; or a salt or solvate thereof

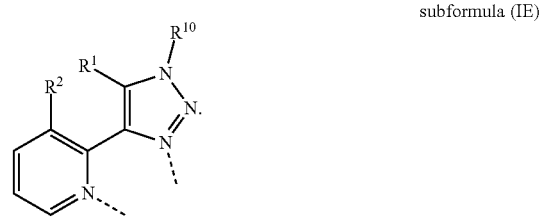

subformula (IE)

19. The compound according to claim 1 of formula (VI)

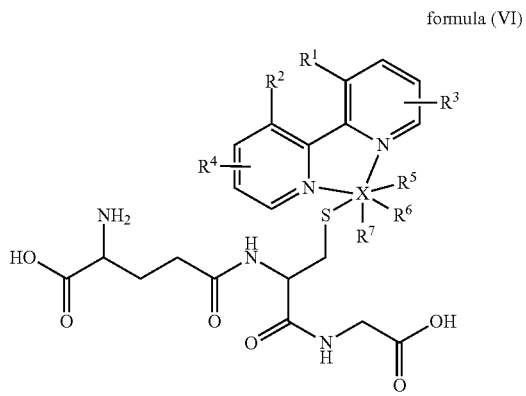

formula (VI)

wherein:

X is selected from platinum and rhenium;

R¹ and R² are independently hydrogen or a substituent selected from C₁₋₄alkyl, halo, haloC₁₋₄alkyl, hydroxy, hydroxyC₁₋₄alkyl, C₁₋₄alkoxy, C₁₋₄alkoxyC₁₋₄alkyl, nitro, nitroC₁₋₄alkyl, amino, C₁₋₄alkylamino, bis(C₁₋₄alkyl)amino, aminoC₁₋₄alkyl, C₁₋₄alkylaminoC₁₋₄alkyl and bis(C₁₋₄alkyl)aminoC₁₋₄alkyl;

R¹ and R² together with the atoms to which they are attached together form a ring system optionally substituted by 1 or 2 substituents independently selected from R¹¹ wherein R¹¹ at each occurrence, is selected from hydrogen, optionally substituted C₁₋₄alkyl, optionally substituted aryl and optionally substituted heteroaryl;

R³ and R⁴ are independently hydrogen or a substituent selected from C₁₋₄alkyl, halo, haloC₁₋₄alkyl, hydroxy, hydroxyC₁₋₄alkyl, C₁₋₄alkoxy, C₁₋₄alkoxyC₁₋₄alkyl, nitro, nitroC₁₋₄alkyl, amino, C₁₋₄alkylamino, bis(C₁₋₄alkyl)amino, aminoC₁₋₄alkyl, C₁₋₄alkylaminoC₁₋₄alkyl and bis(C₁₋₄alkyl)aminoC₁₋₄alkyl; and R⁵, R⁶ and R are each independently selected from optionally substituted C₁₋₄alkyl, optionally substituted aryl, optionally substituted heteroaryl and —CO.

20. The compound according to claim 1 selected from:
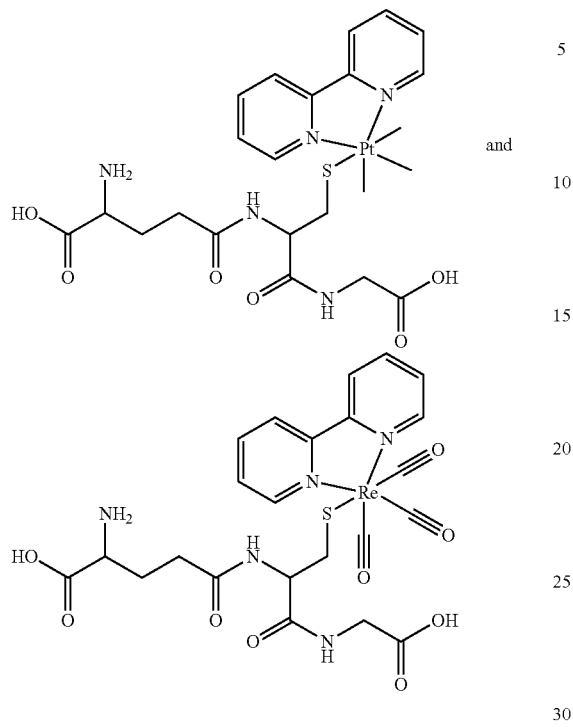
or a salt or solvate thereof.
21. The compound of claim 1 wherein $R^8$ is glutathione.
* * * * *